United States Patent [19]

Grollier et al.

[11] Patent Number: 4,765,976

[45] Date of Patent: Aug. 23, 1988

[54] METHOD FOR COMBATING THE GREASY APPEARANCE OF HAIR

[75] Inventors: Jean F. Grollier; Chantal Fourcadier, both of Paris; Claude Dubief, Le Chesnay, all of France

[73] Assignee: L'Oreal, Paris, France

[21] Appl. No.: 37,014

[22] Filed: Apr. 10, 1987

[30] Foreign Application Priority Data

Apr. 18, 1986 [FR] France .............................. 86 05659

[51] Int. Cl.$^4$ ..................... A61K 7/06; A61K 31/73
[52] U.S. Cl. ........................................ 424/70; 424/71;
424/DIG. 1; 424/DIG. 2; 514/55; 514/880;
514/881
[58] Field of Search ....................... 514/55, 880, 881;
424/70, 71, DIG. 1, DIG. 2

[56] References Cited

U.S. PATENT DOCUMENTS 3,879,376  4/1975  Vanlerberghe et al. ......... 424/47 X
4,528,283  7/1985  Lang et al. ..................... 514/881 X

FOREIGN PATENT DOCUMENTS 0097229  1/1984  European Pat. Off. .
2137684  12/1972  France .

Primary Examiner—Nicky Chan
Assistant Examiner—Wendy B. Davis
Attorney, Agent, or Firm—Cushman, Darby & Cushman

[57] ABSTRACT

The invention relates to a cosmetic composition for combating the greasy appearance of hair. This composition is characterized in that it contains an active product consisting of a particular polymer derived from chitosan comprising 0 to 30% by weight of units (A), 5 to 50% by weight of units (B), 30 to 90% by weight of units (C), or alternatively preferably 0 to 20% by weight of units (A), 40 to 50% by weight of units (B), 40 to 50% by weight of units ($C_1$) below;

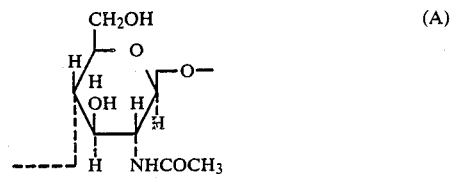

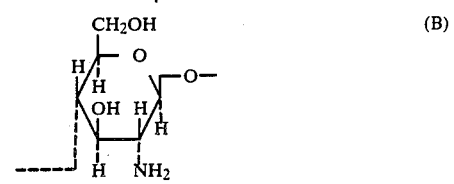

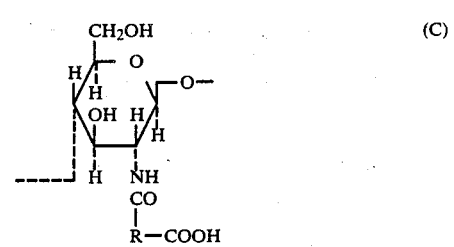

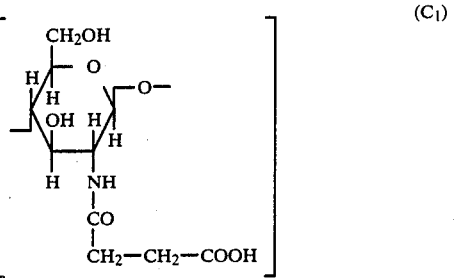

The use of the composition makes it possible to delay the onset of the greasy appearance of the hair.

8 Claims, No Drawings

METHOD FOR COMBATING THE GREASY APPEARANCE OF HAIR

The present invention relates to a cosmetic composition for combating the greasy appearance of hair, and more especially a cosmetic composition by means of which the onset of the greasy appearance of the hair may be delayed or by means of which the period during which the hair does not appear greasy may be extended.

These compositions contain at least one particular polymer derived from chitosan.

The subject of the invention is also the use of a polymer derived from chitosan for treating hair, enabling the greasy appearance of the hair to be combated and, in particular, enabling the onset of its greasy appearance to be delayed.

The hair of some people has a greasy and unattractive appearance as a result of an excessively copious secretion of the sebaceous glands. Such people are commonly said to have "greasy" hair.

French patent No. 2,137,684 and also U.S. Pat. No. 3,879,376 teach the preparation of polymers derived from chitosan, as well as the use of their film-forming and humectant property in cosmetic compositions for the skin.

European patent application No. 97,229 teaches the use of glycerolated derivatives of chitosan in compositions for treating the skin or hair; however, combating the greasy appearance of the hair is not mentioned in said European patent application.

While continuing its research on the use of these chitosan derivatives, the Applicant discovered that some polymers derived from chitosan possessed the property of combating the greasy appearance of hair, and in particular of delaying the time at which the hair appears "greasy".

The subject of the invention is a cosmetic composition designed to combat the greasy appearance of hair, characterized in that it contains, in a suitable cosmetic vehicle, at least one particular polymer derived from chitosan and incorporating monomeric units B and C or A, B and C or B and $C_1$ or A, B and $C_1$, in the proportions stated below.

It is appropriate to note that the composition according to the invention does not appear to affect the production of sebum, but affects, in particular, the appearance of the hair which, despite the production of sebum, appears less "greasy". In other words, a longer period elapses between washing the hair and the onset of the "greasy" appearance when a composition containing a particular class of polymers derived from chitosan is applied to the hair, as will be described below.

The subject of the invention is hence a cosmetic composition containing, as active ingredient, at least one particular polymer derived from chitosan incorporating the monomeric units B and C or A, B and C, corresponding to the following formulae:

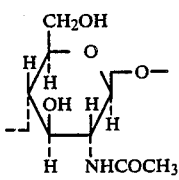
(A)

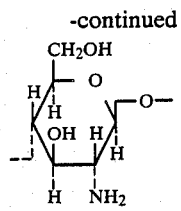
(B)

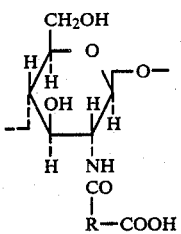
(C)

in which the unit A is present in proportions of between 0 and 30% by weight, the unit B is present in proportions of between 5 and 50% by weight and the unit C is present in proportions of between 30 and 90% by weight based on to the total weight of said polymer.

In the formula C, R denotes a radical of the formula:

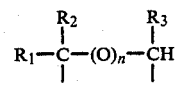

where n denotes zero or 1. When n denotes zero, $R_1$, $R_2$ and $R_3$, which may be identical or different, each denote a hydrogen atom, a methyl, hydroxyl, acetoxy or amino group, an alkylthio residue in which the alkyl group bears an amino group, or a monoalkylamine or dialkylamine residue; it being possible for the monoalkylamine and dialkylamine residues to be interrupted by one or more nitrogen atoms and/or substituted with one or more amine, hydroxyl, carboxyl, alkylthio or sulphonic groups, at least one of the radicals $R_1$, $R_2$ and $R_3$ in this case being a hydrogen atom. When n denotes 1, each of $R_1$, $R_2$ and $R_3$ denotes a hydrogen atom.

The polymers composed of units A, B and C or B and C above can also take the form of a salt formed with a base or with an acid.

The polymers derived from chitosan which are usable in the compositions according to the invention can be prepared by acylation of chitosan with an acid anhydride, in accordance with the procedure described in Example 1 of French patent No. 2,137,684 or in U.S. Pat. No. 3,879,376.

A polymer derived from chitosan, which is more especially preferred according to the invention, incorporates from 0 to 20% by weight of units (A), from 40 to 50% by weight of units (B) and from 40 to 50% by weight of units (C1), this latter unit having the formula:

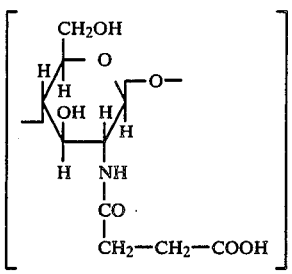

$(C_1)$

This preferred polymer containing units A, B and $C_1$ will be designated polymer $P_1$ in the examples.

The subject of the invention is also a cosmetic composition for treating hair, containing, in a suitable vehicle, at least one polymer derived from chitosan and incorporating (1) from 0 to 30% by weight of unit A, (2) between 5 and 50% by weight of unit B and (3) between 30 and 90% by weight of unit C, or alternatively (1) between 0 and 20% by weight of unit A, (2) between 40 and 50% by weight of unit B and (3) between 40 and 50% by weight of unit $C_1$.

The subject of the invention is also the use of a polymer derived from chitosan and incorporating (1) from 0 to 30% by weight of unit A, (2) from 5 to 50% by weight of unit B and (3) from 30 to 90% by weight of unit (C), or alternatively (1) from 0 to 20% by weight of unit A, (2) from 40 to 50% by weight of unit B and (3) from 40 to 50% by weight of unit $C_1$.

The content of polymer derived from chitosan in the cosmetic compositions according to the invention can generally vary from 0.1 to 5% by weight, and more especially from 0.25 to 2% by weight, relative to the total weight of the composition. The vehicle used in the compositions of the invention must be capable of dissolving the polymer used as an active ingredient. The vehicle customarily used is selected from the group consisting of water and a mixture of water and alcohol (aqueous-alcoholic mixture), in which the alcohol is preferably an alkanol having from 1 to 4 carbon atoms. Ethanol or isopropyl alcohol is preferred. When the vehicle is an aqueous-alcoholic mixture, the alcohol is present in proportions equal to or less than 55% by weight relative to the total weight of the composition. The compositions of the invention can contain, in addition to the polymer derived from chitosan, one or more additives chosen from the group consisting of surfactants, perfumes, colourings, preservatives, sequestering agents, foam stabilizers, ultraviolet radiation-absorbing agents and peptizing agents. The compositions can contain in addition the other additives customarily used in cosmetic compositions.

The subject of the invention is also the above-mentioned cosmetic compositions, packaged industrially in a suitable pack and with a direction leaflet containing written instructions for using the compositions for the purpose of delaying the onset of the greasy appearance of the hair.

The compositions according to the invention can take the form of non-rinsed products, such as styling lotions, sprays or foams, shaping lotions, sprays or foams, setting lotions, sprays or foams or blow-drying lotions, sprays or foams, which are prepared according to the usual methods.

The compositions according to the invention also take the form of shampoos, lotions, foams or sprays to be rinsed, forming treatment products capable of being applied before or after dyeing or bleaching, before or after shampooing and before or after permanent waving.

The pH of these compositions can vary from 3 to 10, and is preferably below 7.

When the compositions take the form of pressurized compositions to form aerosols, sprays or foams, they contain a propellant in addition. As propellants, there may be used, in particular, carbon dioxide, nitrogen, nitrous oxide, volatile hydrocarbons such as butane, isobutane or propane, or preferably chlorinated and/or fluorinated hydrocarbons.

The subject of the invention is also the use of the particular polymer derived from chitosan, defined above, in the treatment of hair for the purpose of delaying the onset of its "greasy" appearance.

The subject of the invention is also a method for the treatment of hair by means of which the "greasy" appearance of the hair may be combated, consisting in applying to the hair an effective amount of a composition containing at least one particular chitosan derivative defined above.

The application of the composition is advantageously carried out immediately after washing the hair using a shampoo, or a short time after this shampooing. After impregnation of the hair with the composition containing the polymer derived from chitosan, the hair can be dried directly (in the case of the non-rinsed compositions). It is also possible to perform rinsing before drying the hair (in the case of the rinsed compositions). Naturally, it is possible to set the hair before drying it.

The application of a composition according to the invention to the hair can also consist in washing the hair with a shampoo containing the particular polymer derived from chitosan. It is then appropriate to leave the shampoo on the hair for a few minutes before rinsing it.

Other subjects of the invention will emerge on reading the examples, in which the parts and percentages are expressed by weight except where otherwise stated.

EXAMPLE 1

An anti-grease lotion of the following formula is prepared:

| | |
|---|---|
| Polymer of formula ($P_1$) | 0.5 g AS |
| Ethanol | 10.0 g |
| Perfume qs | |
| Colouring qs | |
| Preservative qs | |
| Lactic acid qs pH 3.5 | |
| Water qs | 100 g |

(AS = active substance)

EXAMPLE 2

The anti-grease shampoo of the following formula is prepared:

| | |
|---|---|
| Sodium lauryl ether sulphate | 8.0 g AS |
| Polymer of formula ($P_1$) | 1.0 g AS |
| Perfume qs | |
| Colouring qs | |
| Preservative qs | |
| Triethanolamine qs pH 6 | |
| Water qs | 100 g |

EXAMPLE 3

An anti-grease shampoo having the following composition is prepared:

| | |
|---|---|
| Ammonium lauryl sulphate | 8.0 g |
| Polymer of formula P₁ | 1.0 g |
| Water qs | 100 g |
| pH adjusted to 6.0 | |

We claim:

1. A method for combating the greasy appearance of hair comprising applying to the hair in an amount to combat effectively the greasy appearance of the hair a cosmetic composition containing in a cosmetically acceptable vehicle at least one polymer derived from chitosan comprising monomeric units of the formulae:

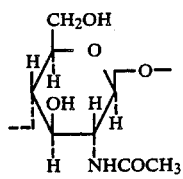 (A)

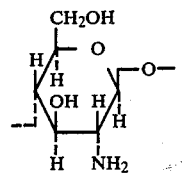 (B)

and

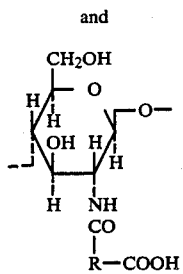 (C)

wherein the unit A is present in an amount rnaging from 0 to 30 weight percent, the unit B is present in an amount ranging from 5 to 50 weight percent and the unit C is present in an amount ranging from 30 to 90 weight percent, based on the total weight of said polymer, R represents a radical of the formula

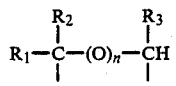

n represents 0 or 1, when n represents O, $R_1$, $R_2$ and $R_3$ each independently represent hydrogen; methyl; hydroxyl; acetoxy; amino; alkylthio wherein the alkyl moiety bears an amino group; monoalkylamine; dialkylamine; monoalkylamine substituted with one or more amine, hydroxyl, carboxyl, alkylthio or sulphonic groups in which case at least one of $R_1$, $R_2$, and $R_3$ is hydrogen; or dialkylamine substituted with one or more amine, hydroxyl, carboxyl, alkylthio or sulphonic groups in which case at least one of $R_1$, $R_2$ and $R_3$ is hydrogen; and when n represents 1, each of $R_1$, $R_2$ and $R_3$ represents hydrogen; or a salt formed by the said chitosan derivative with a base or acid.

2. The method of claim 1 wherein said chitosan derivative consists of 0 to 20 weight percent of unit A, from 40 to 50 weight percent of unt B and from 40 to 50 weight percent of unit $C_1$ having the formula:

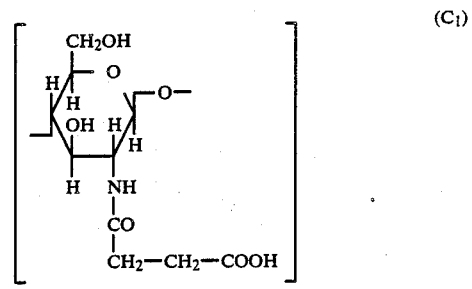 ($C_1$)

3. The method of claim 1 wherein said polymer derived from chitosan or said salt formed by the said chitosan derivative with a base or acid is present in an amount ranging from 0.1 to 5 percent by weight based on the total weight of said composition.

4. The method of claim 1 wherein said cosmetically acceptable vehicle is water or a mixture of water and an alcohol having 1–4 carbon atoms, said alcohol being present in an amount equal to or less than 55 percent by weight based on the total weight of the composition.

5. The method of claim 4 wherein said vehicle is said mixture of water and alcohol, and said alcohol is ethanol or isopropanol.

6. The method of claim 1 wherein said coposition also contains one or more of a surfactant, a perfume, a coloring agent, a preservative, a sequestering agent, a foam stabilizer, an ultraviolet radiation absorbing agent and a peptizing agent.

7. The method of claim 1 wherein said composition is a non-rinsed spray or foam composition in the form of a hair styling lotion, a hair shaping lotion, a hair setting lotion, or a hair blow-drying lotion.

8. The method of claim 1 wherein said composition is a composition to be rinsed from the hair in the form of a shampoo or in the form of a spray or foam lotion, capable of being applied to the hair before or after dyeing or bleaching the hair or before or after shampooing the hair or before or after permanent waving the hair.

* * * * *